United States Patent
Park et al.

(10) Patent No.: US 10,588,842 B2
(45) Date of Patent: Mar. 17, 2020

(54) USE OF SILICONE FLUIDS AS INSECTICIDES

(71) Applicant: PARK AND PARK, Closter, NJ (US)

(72) Inventors: John Y. Park, Closter, NJ (US); Dong W. Park, Whitestone, NY (US)

(*) Notice: Subject to any disclaimer, the term of this patent is extended or adjusted under 35 U.S.C. 154(b) by 504 days.

(21) Appl. No.: 15/039,597

(22) PCT Filed: Jan. 2, 2015

(86) PCT No.: PCT/US2015/010036
§ 371 (c)(1),
(2) Date: May 26, 2016

(87) PCT Pub. No.: WO2015/103471
PCT Pub. Date: Jul. 9, 2015

(65) Prior Publication Data
US 2017/0258696 A1    Sep. 14, 2017

Related U.S. Application Data

(60) Provisional application No. 61/922,953, filed on Jan. 2, 2014.

(51) Int. Cl.

| | | |
|---|---|---|
| *A61K 36/00* | (2006.01) | |
| *A61K 8/58* | (2006.01) | |
| *A01N 65/42* | (2009.01) | |
| *A61Q 17/02* | (2006.01) | |
| *A61K 8/92* | (2006.01) | |
| *A01N 25/02* | (2006.01) | |
| *A61K 31/695* | (2006.01) | |
| *A01N 25/06* | (2006.01) | |
| *A01N 25/16* | (2006.01) | |
| *A01N 55/00* | (2006.01) | |
| *A01N 65/06* | (2009.01) | |
| *A61K 8/04* | (2006.01) | |
| *A61K 8/06* | (2006.01) | |

(52) U.S. Cl.
CPC .............. *A61K 8/585* (2013.01); *A01N 25/02* (2013.01); *A01N 25/06* (2013.01); *A01N 25/16* (2013.01); *A01N 55/00* (2013.01); *A01N 65/06* (2013.01); *A01N 65/42* (2013.01); *A61K 8/046* (2013.01); *A61K 8/06* (2013.01); *A61K 8/92* (2013.01); *A61K 8/922* (2013.01); *A61K 31/695* (2013.01); *A61Q 17/02* (2013.01); *Y02A 50/322* (2018.01); *Y02A 50/324* (2018.01); *Y02A 50/37* (2018.01)

(58) Field of Classification Search
None
See application file for complete search history.

(56) References Cited

U.S. PATENT DOCUMENTS

| | | |
|---|---|---|
| 6,168,782 B1 | 1/2001 | Lin et al. |
| 2005/0101566 A1 | 5/2005 | Burgess et al. |
| 2011/0251070 A1* | 10/2011 | Poffenberger ......... A01N 25/30 504/358 |
| 2012/0171313 A1* | 7/2012 | Boone .................... A01N 65/00 424/769 |

OTHER PUBLICATIONS

Authorized Officer: Lee W. Young, "International Search Report and Written Opinion", issued in counterpart International Application No. PCT/US15/10036, dated Apr. 3, 2015, Publisher: PCT, Published in: WO.

* cited by examiner

*Primary Examiner* — Qiuwen Mi
(74) *Attorney, Agent, or Firm* — Kaplan Breyer Schwarz, LLP

(57) ABSTRACT

Compositions and methods for treating and preventing arthropod infestation are disclosed. A method of treating an arthropod infestation in a subject in need thereof, the method comprising administering topically to the subject an effective amount of either an insecticidal composition consisting essentially of at least one essential oil and a pentacyclosiloxane or an insecticidal composition comprising at least one essential oil, a pentacyclosiloxane, and a mineral oil.

17 Claims, No Drawings

USE OF SILICONE FLUIDS AS INSECTICIDES

RELATED APPLICATION

This application is a national phase of PCT application No. PCT/US2015/010036, filed on Jan. 2, 2015, which claims the benefit of U.S. Provisional Application No. 61/922,953, filed on Jan. 2, 2014. The entire teachings of the above application are incorporated herein by reference.

BACKGROUND OF THE INVENTION

Many insects, such as bed bugs, lice, fleas, ticks, mosquitos, mites, ants, termites, and cockroaches, may infest the bodies and homes of humans and animals. The bite of these insects may cause the infested subject to scratch and break the skin, allowing bacteria to enter the body and possibly causing a serious bacterial infection. In other instances, these and other insects may cause structural harm to homes and buildings as well as cause unsightliness to humans.

To treat or prevent infestation, many people rely on insecticides and insect repellents. Numerous insecticides and insect repellents now exist on the market. Unfortunately, these options suffer from two notable shortcomings. First, many chemicals used in insecticides and repellents are also highly toxic to wildlife, and widespread use of these insecticides can create significant environmental and health hazards.

Second, insects may develop a resistance to an insecticide by producing large amounts of enzymes, such as esterases which either break down the insecticide molecule or bind to it so tightly that it cannot function. Alternatively, insects may mutate at the insecticide target site, which will block the action of the insecticide. Consequently, some commercially available insecticides rely on adding a secondary insecticide to the composition to hinder insect adaptation.

SUMMARY OF THE INVENTION

Currently, there is still a need for an insecticide that does not suffer from the above-identified shortcomings.

In an example embodiment, the present invention is a method of treating an arthropod infestation in a subject in need thereof, the method comprising administering topically to the subject an effective amount of an insecticidal composition consisting essentially of at least one essential oil and a pentacyclosiloxane represented by formula (I):

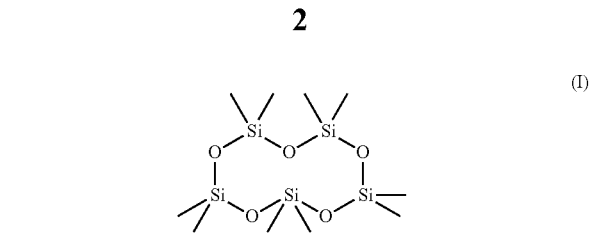

In another embodiment, the present invention is a method of treating an arthropod infestation in a subject in need thereof, the method comprising administering topically to the subject an effective amount of an insecticidal composition consisting essentially of at least one essential oil, a pentacyclosiloxane represented by formula (I):

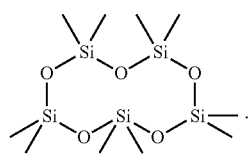

and a mineral oil.

In another embodiment, the present invention is a method of killing an arthropod at a target site, the method comprising applying, e.g., in the form of a spray or as a fogging formulation, to the target site an effective amount of an insecticidal composition consisting essentially of at least one essential oil and a pentacyclosiloxane represented by formula (I):

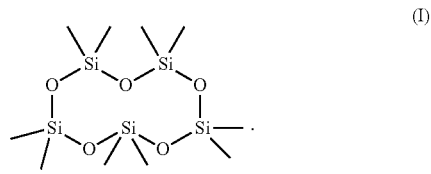

In another embodiment, the present invention is a method of killing an arthropod at a target site, the method comprising applying, e.g., in the form of a spray or as a fogging formulation, to the target site an effective amount of an insecticidal composition consisting essentially of at least one essential oil, a pentacyclosiloxane represented by formula (I):

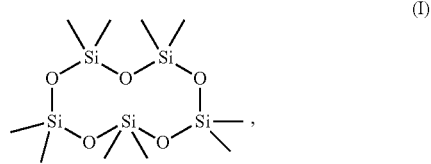

and a mineral oil.

In another embodiment, the present invention is a method of treating an arthropod infestation in a subject in need thereof, the method comprising administering topically to the subject an effective amount of an insecticidal composition consisting essentially of at least one essential oil, a pentacyclosiloxane represented by formula (I):

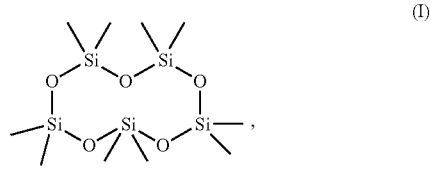

and
wherein the insecticidal composition does not include cedar oil or neem oil.

In another embodiment, the present invention is a method of treating an arthropod infestation in a subject in need thereof, the method comprising administering topically to the subject an effective amount of an insecticidal composition consisting essentially of at least one essential oil, a pentacyclosiloxane represented by formula (I):

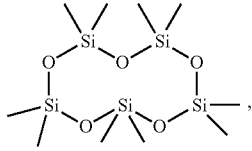

and
a mineral oil, and wherein the insecticidal composition does not include cedar oil or neem oil.

In another embodiment, the present invention is a method of killing an arthropod at a target site, the method comprising applying to the target site an effective amount of an insecticidal composition consisting essentially of at least one essential oil, and a pentacyclosiloxane represented by formula (I):

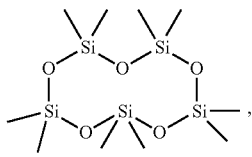

and
wherein the insecticidal composition does not include cedar oil or neem oil.

In another embodiment, the present invention is a method of killing an arthropod at a target site, the method comprising applying to the target site an effective amount of an insecticidal composition consisting essentially of at least one essential oil, and a pentacyclosiloxane represented by formula (I):

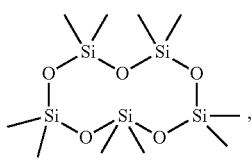

and
a mineral oil, and wherein the insecticidal composition does not include cedar oil or neem oil.

In another embodiment, the present invention is a composition consisting essentially of at least one essential oil and a pentacyclosiloxane represented by formula (I):

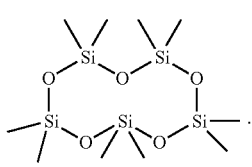

In another embodiment, the present invention is a composition consisting essentially of at least one essential oil and a pentacyclosiloxane represented by formula (I):

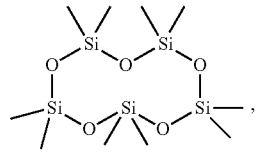

and
a mineral oil.

In another embodiment, the present invention is a composition consisting essentially of at least one essential oil, and a pentacyclosiloxane represented by formula (I):

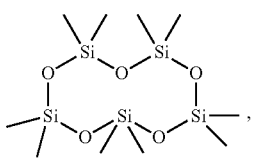

and
wherein the insecticidal composition does not include cedar oil or neem oil.

In another embodiment, the present invention is a composition consisting essentially of at least one essential oil, a pentacyclosiloxane represented by formula (I):

and
a mineral oil, and wherein the insecticidal composition does not include cedar oil or neem oil.

In another embodiment, the present invention is a method of repelling an arthropod, the method comprising applying to a subject or surface the composition of any of the above embodiments in an amount sufficient to repel said arthropod.

The compositions and methods of the present invention effectively kill arthropods within minutes after contact. The present invention does not rely on toxic chemicals and is safe for use directly on human or animal skin.

DETAILED DESCRIPTION OF THE INVENTION

As used herein, the term "arthropod" refers to members of the arthropod phyllum, including insects, arachnids, and crustaceans. Examples include, but are not limited to, lice, bed bugs, fleas, flies, gnats, midges, ticks, mosquitos, mites, ants, cockroaches, spiders, scorpions, termites, bees, wasps, stored product pests, carpet beetles, centipedes, crickets, drugstore beetles, earwigs, book lice, silverfish, *Armadillidum vulgare*, *Porcellio laevis*, and *Uroblaniulus jersey*.

As used herein, the term "diluent" refers to all inert vehicles, carriers, excipients, or solvents added to a composition to provide, without limitation, bulk, consistency, stability, binding ability, lubrication, etc., to the composition. Multiple diluents may be mixed together if desired.

As used herein, an "effective amount" refers to an amount of an agent or a combination of agents that is sufficient to treat, control, or prevent the undesired condition, such as, infestation by arthropods. Examples of effective amounts of the cyclic polysiloxane described herein for use on a surface, including human or animal skin, range from about 0.05 fl. oz/in$^2$ to about 0.1 fl. oz/in$^2$. Examples of effective amounts for use in a target volume range from about 6 fl. oz/1,000 ft$^3$ to about 10 fl. oz/1,000 ft$^3$.

As used herein, an "essential oil" refers to a concentrated hydrophobic liquid compound extracted from plants. Examples include, but are not limited to, aloe vera oil, allspice oil, anisum oil, basil oil, cajeput oil, catnip oil, cedar oil, chrysanthemum oil, cinnamon oil, citronella oil, clove oil, eucalyptus oil, garlic oil, geranium oil, lavender oil, marjoram oil, melaleuca oil, neem oil, pennyroyal oil, peppermint oil, pine oil, rosemary oil, sage oil, spearmint oil, thyme oil or any other members of the mint (Lamiaceae or Labiatae) family, tea-tree oil, vanilla oil, and verbena oil.

As used herein, an "insecticide" refers to a compound or composition used to kill, control, or prevent the growth of arthropods.

As used herein, a "mineral oil" refers to a refined hydrocarbon oil without animal or vegetable additives and can include aliphatic, napthenic, aromatic, and/or paraffinic components.

As used herein, a "repellent" refers to a compound or composition which reduces or eliminates voluntary contact of an arthropod with a surface on which the composition is present in comparison to a surface on which the composition is absent. As used herein, the term "repelling" refers to application of a compound or composition which reduces or eliminates voluntary contact of an arthropod with a surface on which the composition is present in comparison to a surface on which the composition is absent.

As used herein, the term "subject" refers to a mammal, for example a human, but can also mean an animal in need of veterinary treatment, e.g., companion animals (e.g., dogs, cats, and the like), farm animals (e.g., cows, sheep, pigs, horses, and the like), and laboratory animals (e.g., rats, mice, guinea pigs, and the like).

As used herein, a "target site" refers to a location suitable for applying an insecticide or repellent.

As used herein, the term "topical" refers a mode of application of a composition whereby the composition is applied to any external parts of a mammal, such as humans, horses, cats, and dogs, and includes skin and hair.

As used herein, the terms "treating," "treat," or "treatment" describe the management and care of a subject for the purpose of combating a condition and includes administration of a therapeutic agent or a combinations of therapeutic agents to alleviate or eliminate the symptoms of a condition.

As used herein, the term "bed bugs" refers to members of the genus *Cimex*, including, for example, members of the species *Cimex lectularius*, and *Cimex hemipterus*.

As used herein, the term "termite" refers to members of the order Isoptera, including, for example, members of the species *Reticulitermes flavipes, Reticulitermes virginicus, Reticulitermes tibialis, Reticulitermes hesperus, Reticulitermes humilis, Incisitermes minor*, and *Marginitermes hubbardi*.

As used herein, the term "cockroach" refers to members of the order Blattodea, including, for example, members of the species *Blatella germanica, Periplaneta americana, Periplaneta brunnea*, and *Blatta orientalis*.

As used herein, the term "ant" refers to members of the family Formicidae, including, for example, members of the species *Monomorium minimum, Camponotus herculeanus pennsylvanicus, Wasmannia auropunctata, Iridomyrmex humilis*, and *Monomorium pharaonis*.

As used herein, the term "lice" refers to members of the order Phthiraptera, including, for example, members of the species *Pediculus capitis, Pediculus humanus*, and *Pthirus pubis*.

As used herein, the term "flea" refers to members of the family Pulicidae, including, for example, members of the species *Ctenocephalides felis, Ctenocephalides canis*, and *Pulex irritans*.

As used herein, the term "mosquito" refers to members of the family Culicidae, including, for example, members of the species *Culex pipiens, Aedes aegypti*, and *Andopheles quadrimaculatus*.

As used herein, the term "mite" refers to members of the family Acaridae, including, for example, members of the species *Acarus siro, Tyrophagus longior*, and *Glycyphagus domesticus*.

As used herein, the term "tick" refers to members of the orders Ixodida and Parasitiformis, including, for example, members of the species *Rhipicephalus sanguineus, Ixodes cookei, Ornithodoros hermsi*, and *Dermacentor variabilis*.

As used herein, the terms "flies" "gnats," and "midges" refer to members of the order Diptera, including, for example, members of the species *Musca domestica, Phormia regina, Musca autumnalis, Stomoxys calcitrans, Musca stabulans, Calliphora vomitoria, Pollenia rudis, Drosophilia melanogaster, Scenopinus fenestralis, Culicoides mississippiensis, Psychoda pacifica, Psychoda alternate, Ceratopogonidae stellifer, Chironomus plumosus*, and *Phaenicia sericata*.

As used herein, the terms "bees" and "wasps" refer to members of the families Apidae and Vespidae, including, for example, members of the species *Apis mellifera, Xylocopa virginica, Dolichovespula arctica*, and *Vespula pensylvanica*.

As used herein "stored product pest" refers to members of the families Laemophloeidae, Gelechiidae, and Nitidulidae, including, for example, members of the species *Carpophilus hemipterus, Sitotroga cerealella*, and *Cryptolestesp pusillus*.

As used herein, the term "carpet beetle" refers to members of the family Dermestidae, including, for example, members of the species *Anthrenus scrophulariae*.

As used herein, the term "centipede" refers to members of the order Scutigeromorpha, including, for example, members of the species *Scutigera coleoptrata*.

As used herein, the term "cricket" refers to members of the order Orthoptera, including, for example, members of the species *Acheta domesticus*.

A used herein, the term "drugstore beetle" refers to members of the family Anobiidae, including, for example, members of the species *Stegobium paniceum*.

As used herein, the term "earwig" refers to members of the order Dermaptera, including, for example, members of the species *Forficula auricularia*.

As used herein, the term "book lice" refers to members of the order Psocoptera, including, for example, members of the species *Trogium pulsatorium*.

As used herein, the term "silverfish" refers to members of the order Thysanura, including, for example, members of the species *Lepisma saccharina*.

As used herein, the term "spider" refers to members of the order Aranae, including, for example, members of the species *Achaearanea tepidariorum, Dolomedes tenebrosus, Lycosa helluo, Coras medicinalis, Salticus scenicus, Pholcus phalangioides*, and *Spermophora meridionalis*.

As used herein, the term "silicone fluid" refers to any liquid polysiloxane.

As used herein, the term "polysiloxane" refers to a polymer having a structural unit of:

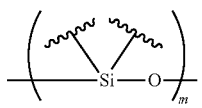

wherein the polymer can be linear or cyclic, the Si atom is attached to at least one organic moiety at the position indicated by "⌇⌇", and m is an integer of at least 2.

As used herein, the term "alkyl," unless otherwise indicated, means straight or branched saturated monovalent hydrocarbon radicals of formula $C_pH_{2p+1}$. In one embodiment, p is an integer from 1 to 18. In another embodiment, p is an integer from 1 to 12. In another embodiment, p is an integer from 1 to 6. Alkyl can optionally be substituted with —OH, —SH, halogen, amino, cyano, nitro, a $C_1$-$C_{12}$ alkyl, $C_1$-$C_{12}$ haloalkyl, $C_1$-$C_{12}$ alkoxy, $C_1$-$C_{12}$ haloalkoxy, or $C_1$-$C_{12}$ alkyl sulfanyl. In some embodiments, alkyl can optionally be substituted with one or more halogen, hydroxyl, $C_1$-$C_{12}$ alkyl, $C_1$-$C_{12}$ alkenyl or $C_1$-$C_{12}$ alkynyl group, $C_1$-$C_{12}$ alkoxy, or $C_1$-$C_{12}$ haloalkyl. The term alkyl can also refer to cycloalkyl.

The term "cycloalkyl", as used herein, means saturated cyclic hydrocarbons, i.e. compounds where all ring atoms are carbons. In some embodiments, a cycloalkyl comprises from 3 to 18 carbons. In other embodiments, a cycloalkyl comprises from 3 to 6 carbons. Examples of cycloalkyl include, but are not limited to, cyclopropyl, cyclobutyl, cyclopentyl, cyclohexyl, and cycloheptyl. Substitutions and preferred substitutions for cycloalkyl are defined above with respect to "alkyl."

The term "haloalkyl," as used herein, includes an alkyl substituted with one or more F, Cl, Br, or I, wherein alkyl is defined above.

The terms "alkoxy," as used herein, means an "alkyl-O—" group, wherein alkyl is defined above. Examples of alkoxy groups include methoxy or ethoxy groups.

The term "aryl," as used herein, refers to a carbocyclic aromatic group. Preferably, an aryl comprises from 6 to 18 carbons. Examples of aryl groups include, but are not limited to phenyl and naphthyl. Examples of aryl groups include optionally substituted groups such as phenyl, biphenyl, naphthyl, phenanthryl, anthracenyl, pyrenyl, fluoranthyl or fluorenyl. An aryl can be optionally substituted. Examples of suitable substituents on an aryl include halogen, hydroxyl, $C_1$-$C_{12}$ alkyl, $C_1$-$C_{12}$ alkene or $C_1$-$C_{12}$ alkyne, $C_3$-$C_{12}$ cycloalkyl, $C_1$-$C_{12}$ haloalkyl, $C_1$-$C_{12}$ alkoxy, aryloxy, or a $C_6$-$C_{18}$ carbocyclic aromatic group.

The term "heteroaryl," as used herein, refers to aromatic groups containing one or more heteroatoms (O, S, or N). A heteroaryl group can be monocyclic or polycyclic, e.g., a monocyclic heteroaryl ring fused to one or more carbocyclic aromatic groups or other monocyclic heteroaryl groups. The heteroaryl groups of this invention can also include ring systems substituted with one or more oxo moieties. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

The present invention relates to methods and compositions for treating an arthropod infestation in a subject in need thereof or killing arthropods at a target site. In one embodiment, the methods and compositions of the present invention include at least one polysiloxane and an essential oil. In another embodiment, at least one polysiloxane is a liquid cyclic polysiloxane.

In an example embodiment, the polysiloxane is a cyclic polysiloxane represented by formula (II):

wherein $R^1$ and $R^2$, each, independently, can be H, hydroxyl, an optionally substituted $C_1$-$C_{30}$ alkyl, an optionally substituted $C_3$-$C_{30}$ cycloalkyl, an optionally substituted $C_6$-$C_{18}$ aryl, or an optionally substituted $C_5$-$C_{18}$ heteroaryl, and n is an integer from 2 to 20.

In another embodiment, $R^1$ and $R^2$, each, independently, can be H, hydroxyl, an optionally substituted $C_1$-$C_{12}$ alkyl, an optionally substituted $C_3$-$C_6$ cycloalkyl, n is an integer from 2 to 10.

In another embodiment, $R^1$ and $R^2$ are the same, and the values and specific values of the remainder of the variables are as described with respect to formula (II). In another embodiment, $R^1$ and $R^2$ are each a $C_1$-$C_6$ alkyl, n is 5.

In yet another embodiment, $R^1$ and $R^2$ can each be methyl, and the values and specific values for the remainder of the variables are as described with respect to formula (II).

In another embodiment, the cyclic polysiloxane is a pentacyclosiloxane, otherwise known as decamethylcyclopentasiloxane, represented by formula (I):

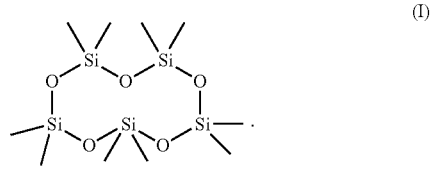

The compositions and methods of the present invention can be used for the treatment of the infestation by arthropods, including insects, arachnids, and crustaceans. Examples of arthropods to be treated by the compositions and methods of the present invention are lice, bed bugs, fleas, gnats, ticks, mosquitos, mites, ants, spiders, scorpions, termites, and cockroaches. In on embodiment, the compositions and methods of the present invention can be used for the treatment of an arthropod selected from the group consisting of lice, bed bugs, fleas, flies, gnats, midges, ticks, mosquitos, mites, ants, cockroaches, spiders, scorpions, termites, bees, wasps, stored product pests, carpet beetles, centipedes, crickets, drugstore beetles, earwigs, book lice, silverfish, *Armadillidum vulgare, Porcellio laevis,* and *Uroblaniulus jersey.*

In another embodiment the arthropod is selected from the group consisting of members of the order Isoptera, Blattodea, Pthiraptera, Ixodida, Parasitiformis, Diptera, Scutigeromorpha, Orthoptera, Dermaptera, Psocoptera, Thysanura, Aranae; members of the family Formicidae, Pulicidae, Culicidae, Acaridae, Apidae, Vespidae, Laemophloeidae, Gelechiidae, Nitidulidae, Dermestidae, Anobiidae; members of the genus *Cimex*; and members of the species *Armadillidum vulgare, Porcellio laevis,* and *Uroblaniulus jersey.*

In another embodiment, the compositions and methods of the present invention can be used for the treatment of the infestation of bed bugs, such as, for examples bed bugs of the species *Cimex lectularius* or *Cimex hemipterus* In another embodiment, the compositions and methods of the present invention can be used for the treatment of the infestation of termites, such as, for example, termites of the order Isoptera.

The compositions of the present invention can be applied to a subject or a target site by any method suitable for applying an insecticide or repellent. Examples of a target site include, but are not limited to, walls, ceilings, mattresses, box springs, bed frames, bed sheets and linens, couches, futons, chairs, door frames, bars, booths, furniture, and plants. The compositions of the present invention can also be used to fill a void or cavity. Examples of a void or cavity include, but are not limited to, areas inside a bar or booth, inside equipment, inside a wall, under a slab, inside a tube, inside hollow furniture, behind shelving or store fixtures, or inside a drawer, drain line or piping.

In another embodiment, the compositions of the present invention can be administered topically to a human or animal subject. Topical embodiments of the invention include, but are not limited to, lotions, ointments, gels, creams, sprays, aerosols, solutions, emulsions, suspensions, or other forms known to one of skill in the art. See, e.g., Remington's Pharmaceutical Sciences (1980 & 1990) 16th and 18th eds., Mack Publishing, Easton Pa. and Introduction to Pharmaceutical Dosage Forms (1985) 4th ed., Lea & Febiger, Philadelphia.

In one embodiment, the compositions of the present invention can be applied via a hydraulic spray. A hydraulic spray converts the compositions into droplets by forcing the compositions of the present invention through a spray nozzle under pressure. Examples of hydraulic sprayers include compressed air sprayers and trigger sprayers.

In another embodiment, the compositions of the present invention can be applied as an aerosol spray. An aerosol spray mixes air into the compositions of the present invention and uses air or a propellant to expel the spray, resulting in smaller particle sizes. In an example embodiment, the particle size is about 50 microns or less. Aerosol sprays can be applied by methods or equipment including in an aerosol can with aerosol generating equipment such as the Actisol® machine.

In other embodiments, the compositions of the present invention can be applied as a fog via a fogging system. A fogging system disperses the compositions of the present invention by forcing the compositions through a nozzle via propellant or pressure, which converts the compositions of the present invention into droplets. Examples of fogging systems include aerosol spray canisters and ultra low volume (ULV) fogging machines.

In another embodiment, the compositions of the present invention may be applied as a foam. Foams can be applied to cavities, such as those in walls or under, behind, or in equipment or appliances. When used in a void or cavity, the foam may also be employed to fill the void. A foam may remain or stick on a surface, including vertical surfaces or the bottom of a horizontal surface.

In some embodiments, the polysiloxane is mixed with an essential oil. In one embodiment, the insecticidal composition comprises at least 25% by weight of a polysiloxane and up to 75% by weight of at least one essential oil.

In another embodiment, the polysiloxane can be present in the amount of 30%, 35% 40%, 45%, 50%, 55%, 60%, 65%, 70%, 75%, 80%, 85%, 90%, 95% by weight.

In another embodiment, the at least one essential oil can be present in the amount 5%, 10%, 15%, 20%, 25%, 30%, 35% 40%, 45%, 50%, 55%, 60%, 65%, 70% by weight.

In one embodiment, the insecticidal compositions consist essentially of a polysiloxane and at least one essential oil.

In another embodiment, the insecticidal compositions consist essentially of pentacyclosiloxane and at least one essential oil.

In one embodiment, the pentacyclosiloxane is present in the amount of 30% to 95% by weight of the insecticidal compositions, and the at least one essential oil is present in the amount of 5% to 70% by weight of the insecticidal compositions.

In one embodiment, the at least one essential oil can be selected from a group consisting of: aloe vera oil, allspice oil, anisum oil, basil oil, cajeput oil, catnip oil, cedar oil, chrysanthemum oil, cinnamon oil, citronella oil, clove oil, eucalyptus oil, garlic oil, geranium oil, lavender oil, marjoram oil, melaleuca oil, neem oil, pennyroyal oil, peppermint oil, pine oil, rosemary oil, sage oil, spearmint oil, thyme oil, tea-tree oil, vanilla oil, verbena oil or combinations thereof.

In another embodiment, the at least one essential oil can be selected from a group consisting of: aloe vera oil, allspice oil, anisum oil, basil oil, cajeput oil, catnip oil, chrysanthemum oil, cinnamon oil, citronella oil, clove oil, eucalyptus oil, garlic oil, geranium oil, lavender oil, marjoram oil, melaleuca oil, neem oil, pennyroyal oil, peppermint oil, pine oil, rosemary oil, sage oil, spearmint oil, thyme oil, tea-tree oil, vanilla oil, verbena oil or combinations thereof.

In one embodiment, the at least one essential oil can be selected from a group consisting of: aloe vera oil, allspice oil, anisum oil, basil oil, cajeput oil, catnip oil, cedar oil, chrysanthemum oil, cinnamon oil, citronella oil, clove oil, eucalyptus oil, garlic oil, geranium oil, lavender oil, marjoram oil, melaleuca oil, pennyroyal oil, peppermint oil, pine oil, rosemary oil, sage oil, spearmint oil, thyme oil, tea-tree oil, vanilla oil, verbena oil or combinations thereof.

In another embodiment, the at least one essential oil can be selected from a group consisting of: aloe vera oil, allspice oil, anisum oil, basil oil, cajeput oil, catnip oil, chrysanthemum oil, cinnamon oil, citronella oil, clove oil, eucalyptus oil, garlic oil, geranium oil, lavender oil, marjoram oil, melaleuca oil, pennyroyal oil, peppermint oil, pine oil, rosemary oil, sage oil, spearmint oil, thyme oil, tea-tree oil, vanilla oil, verbena oil or combinations thereof.

In another embodiment, the at least one essential oil is selected from a group consisting of aloe vera oil and cedar oil.

In another embodiment, the at least one essential oil is aloe vera oil.

In another embodiment, the at least one essential oil is cedar oil.

In another embodiment, the insecticidal compositions do not include cedar oil or neem oil.

In another embodiment, the insecticidal compositions comprise an essential oil, a polysiloxane, and a mineral oil. In another embodiment, the insecticidal composition comprises up to 40% by weight of a mineral oil. In another embodiment, the mineral oil can be present in the amount of 5%, 10%, 15%, 20%, 25%, 30%, or 35% by weight.

In another embodiment, the at least one essential oil is present in the amount of 5% to 70% by weight of the composition, the pentacyclosiloxane of formula (I) is present in the amount of 30% to 95% by weight of the composition, and the mineral oil is present in the amount of 40% or less by weight of the composition.

In another embodiment, the insecticidal composition comprises 10% by weight of an essential oil, 70% by weight of a polysiloxane, and 20% by weight of a mineral oil.

In another embodiment, the insecticidal compositions comprise a polysiloxane, an essential oil, and an optional diluent.

In one embodiment, the diluent can be a foaming surfactant. Foaming surfactants can be nonionic, anionic, or cationic in nature. Examples of useful surfactant types include, but are not limited to the following: alcohol ethoxylates, alcohol ethoxylate carboxylate, amine oxides, alkyl sulfates, alkyl ether sulfate, sulfonates, quaternary ammonium compounds, alkyl sarcosines, betains, and alkyl amides.

In one embodiment, the diluent can be an aerosol propellant. Examples of suitable aerosol propellants include volatile hydrocarbons such as butane, propane, isobutane or mixtures thereof, chloro-fluoro carbons, non-ozone-depleting and fluorocarbon propellants such as 1,1,1,2-tetrafluoroethane and 1,1,1,2,3,3,3-heptafluoropropane.

In one embodiment, the diluent can be an emollient. Emollients have a softening or soothing effect. Examples of suitable emollients include hexyleneglycol, propylene glycol, isostearic acid derivatives, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononoate, isotridecyl isononanoate, myristyl myristate, triisocetyl citrate, octyl dodecanol, sucrose esters of fatty acids, octyl hydroxystearate and mixtures thereof.

In another embodiment, the diluent can be a skin-conditioning agent. Examples of suitable skin-conditioning agents include polypropylene glycol alkoxy ethers (PPG alkyl ethers) having the molecular formula of RO(CH$_2$CHOCH$_3$)$_q$, wherein "R" is a straight-chained or branched C$_4$ to C$_{22}$ alkyl group; and "q" is an integer from 4 to about 50. Other suitable examples of PPG alkyl ethers include PPG stearyl ethers, PPG butyl ether, PPG-15 stearyl ether, PPG-2 butyl ether, PPG-9-13 butyl ether and PPG-40 butyl ether.

In another embodiment, the diluent can be natural, animal, vegetable, or synthetic fats and oils. Examples of suitable oils include avocado oil, linseed oil, almond oil, ibota wax, perilla oil, olive oil, cacao butter, kapok wax, kaya oil, carnauba wax, liver oil, candelilla wax, beef tallow, neat's-foot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shear butter, Chinese tung oil, cinnamon oil, jojoba wax, olive oil, squalane, shellac wax, turtle oil, soybean oil, tea seed oil, camellia oil, evening primrose oil, corn oil, lard, rapeseed oil, Japanese tung oil, rice bran wax, germ oil, horse fat, persic oil, palm oil, palm kernel oil, castor oil, hydrogenated castor oil, castor oil fatty acid methyl ester, sunflower oil, grape oil, bayberry wax, jojoba oil, hydrogenated jojoba ester, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, reduced lanolin, lanolin alcohol, hard lanolin, lanolin acetate, lanolin fatty acid isopropyl ester, polyoxyethylene lanolin alcohol ether, polyoxyethylene lanolin alcohol acetate, lanolin fatty acid polyethylene glycol, polyoxyethylene hydrogenated lanolin alcohol ether, egg yolk oil and the like.

In another embodiment, the diluent can be a gelling agent. A gelling agent increases the viscosity of the composition, thereby limiting the rate of its clearance from the site. The gelling agent can be a natural gelling agent, a synthetic gelling agent and an inorganic gelling agent. Examples of suitable gelling agents include naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, starch, chemically modified starches and the like, semi-synthetic polymeric materials such as cellulose ethers (e.g. hydroxyethyl cellulose, hydroxypropyl cellulose, methyl cellulose, carboxymethyl cellulose, methylhydroxyethylcellulose, methylhydroxypropylcellulose, hydroxypropylmethyl cellulose, hydroxyethylcarboxymethylcellulose, carboxymethylcellulose and carboxymethylhydroxyethylcellulose), guar gum, hydroxypropyl guar gum, soluble starch, cationic celluloses, cationic guars, and the like, and synthetic polymeric materials, such as carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like, acrylic acid/ethyl acrylate copolymers and the carboxyvinyl polymers, which consist essentially of a colloidal water-soluble polyalkenyl polyether crosslinked polymer of acrylic acid crosslinked with a crosslinking agent such as polyallyl sucrose or polyallyl pentaerythritol. Examples include Carbopol® 934, Carbopol® 940, Carbopol® 950, Carbopol® 980, Carbopol® 951 and Carbopol® 981.

In other embodiments, the compositions of the present invention can include an additional agent. Examples of additional agents include steroidal antiinflammatory agent, a nonsteroidal anti-inflammatory drug, an immunosuppressive agent, an insect growth regulator, an immunomodulator, an immunoregulating agent, a hormonal agent, an antibiotic agent, an antifungal agent, an antiviral agent, an antiparasitic agent, a vasoactive agent, a vasoconstrictor, a vasodilator, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a disinfectant, an anesthetic, an antiallergic agent, an alpha hydroxyl acid, lactic acid, glycolic acid, a beta-hydroxy acid, a protein, a peptide, a neuropeptide, a allergen, an immunogenic substance, a haptene, an oxidizing agent, an antioxidant, a dicarboxylic acid, azelaic acid, sebacic acid, adipic acid, fumaric acid, an insecticide, an antiproliferative agent, an anticancer agent, a photodynamic therapy agent, an anti-wrinkle agent, a radical scavenger, a metal oxide (e.g., titanium dioxide, zinc oxide, zirconium oxide, iron oxide), silicone oxide, an anti wrinkle agent, a skin whitening agent, a skin protective agent, a masking agent, an anti-wart agent, a refatting agent, a lubricating agent and mixtures thereof.

In other embodiments, the insecticidal compositions of the present invention can include a chemical insect repellent, such as N,N-diethyl-meta-toluamide (DEET).

The following examples are for the purposes of illustration only and are not intended to be limiting of the invention.

Example 1—Pentacyclosiloxane and Aloe Vera Oil Lotion

This example describes an insecticidal composition containing pentacyclosiloxane (65% by weight) and aloe vera oil (35% by weight).

| Ingredient | Weight % |
| --- | --- |
| Pentacyclosiloxane | 65.0 |
| Aloe Vera Oil | 35.0 |

Example 2—Pentacyclosiloxane and Aloe Vera Oil Lotion with Additives

This example describes an insecticidal composition containing pentacyclosiloxane (65% by weight) and aloe vera oil (24.9% by weight).

| Ingredient | Weight % |
| --- | --- |
| Pentacyclosiloxane | 65.0 |
| Aloe Vera Oil | 24.9 |
| Hexyleneglycol | 10.0 |
| Vitamin E | 0.1 |

Example 3—Pentacyclosiloxane and Aloe Vera Oil Foam

This example describes an insecticidal composition as an aerosol spray containing Pentacyclosiloxane (65% by weight) and aloe vera oil (24.5% by weight). The following composition is prepared by mixing the listed ingredients.

| Ingredient | Weight % |
| --- | --- |
| Cyclopentasiloxane | 65.0 |
| Aloe Vera Oil | 24.5 |
| Propane/Butane | 8.0 |
| PEG-40 stearate | 2.50 |

Example 4—Pentacyclosiloxane, Cedar Oil, and Mineral Oil

This example describes an insecticidal composition containing pentacyclosiloxane (70% by weight), cedar oil (10% by weight), and mineral oil (20% by weight).

| Ingredient | Weight % |
| --- | --- |
| Pentacyclosiloxane | 70.0 |
| Cedar Oil | 10.0 |
| Mineral Oil | 20.0 |

Example 5—Pentacyclosiloxane, Cedar Oil, and Mineral Oil

This example describes an insecticidal composition containing pentacyclosiloxane (60% by weight), cedar oil (10% by weight), and mineral oil (30% by weight).

| Ingredient | Weight % |
| --- | --- |
| Pentacyclosiloxane | 60.0 |
| Cedar Oil | 10.0 |
| Mineral Oil | 30.0 |

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A composition, consisting essentially of:
   at least one essential oil;
   a pentacyclosiloxane represented by formula (I):

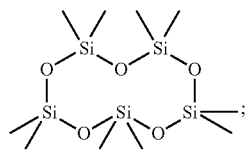

and
   mineral oil;
   wherein the at least one essential oil is present in the amount of 5% to 15% by weight of the composition, the pentacyclosiloxane is present in the amount of 55% to 95% by weight of the composition, and the mineral oil is present in the amount of 5% to 30% by weight of the composition.

2. The composition of claim 1, wherein the at least one essential oil is selected from a group consisting of aloe vera oil, allspice oil, anisum oil, basil oil, cajeput oil, catnip oil, cedar oil, chrysanthemum oil, cinnamon oil, citronella oil, clove oil, eucalyptus oil, garlic oil, geranium oil, lavender oil, marjoram oil, melaleuca oil, neem oil, pennyroyal oil, peppermint oil, pine oil, rosemary oil, sage oil, spearmint oil, thyme oil, tea-tree oil, vanilla oil, and verbena oil.

3. The composition of claim 1, wherein the at least one essential oil is cedar oil.

4. The composition of claim 1, wherein said composition is in the form of an aerosol spray.

5. A composition, consisting essentially of:
at least one essential oil;
a pentacyclosiloxane represented by formula (I):

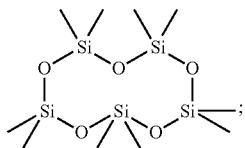

and
mineral oil;
wherein the at least one essential oil is present in the amount of 10% by weight of the composition, the pentacyclosiloxane is present in the amount of 70% by weight of the composition, and the mineral oil is present in the amount of 20% by weight of the composition.

6. The composition of claim 5, wherein the at least one essential oil is cedar oil.

7. The composition of claim 5, wherein the at least one essential oil is selected from a group consisting of aloe vera oil, cedar oil, eucalyptus oil, geranium oil, peppermint oil, rosemary oil, spearmint oil, and thyme oil.

8. A method of killing an arthropod at a target site, the method comprising applying to the target site an effective amount of an insecticidal composition consisting essentially of:
at least one essential oil;
a pentacyclosiloxane represented by formula (I):

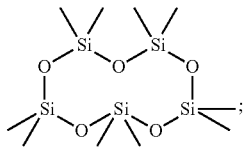

and
mineral oil;
wherein the at least one essential oil is present in the amount of 5% to 15% by weight of the composition, the pentacyclosiloxane is present in the amount of 55% to 95% by weight of the composition, and the mineral oil is present in the amount of 5% to 30% by weight of the composition.

9. The method of claim 8, wherein the at least one essential oil is selected from a group consisting of aloe vera oil, allspice oil, anisum oil, basil oil, cajeput oil, catnip oil, cedar oil, chrysanthemum oil, cinnamon oil, citronella oil, clove oil, eucalyptus oil, garlic oil, geranium oil, lavender oil, marjoram oil, melaleuca oil, neem oil, pennyroyal oil, peppermint oil, pine oil, rosemary oil, sage oil, spearmint oil, thyme oil, tea-tree oil, vanilla oil, and verbena oil.

10. The method of claim 8, wherein the at least one essential oil is selected from the group consisting of aloe vera oil and cedar oil.

11. The method of claim 8, wherein the at least one essential oil is cedar oil.

12. The method of claim 8, wherein the at least one essential oil is present in the amount of 10% by weight of the insecticidal composition, the pentacyclosiloxane of formula (I) is present in the amount of 70% by weight of the insecticidal composition, and the mineral oil is present in the amount of 20% by weight of the insecticidal composition.

13. The method of claim 8, wherein the arthropod is selected from the group consisting of members of the order Isoptera, Blattodea, Pthiraptera, Ixodida, Parasitiformis, Diptera, Scutigeromorpha, Orthoptera, Dermaptera, Psocoptera, Thysanura, Aranae; members of the family Formicidae, Pulicidae, Culicidae, Acaridae, Apidae, Vespidae, Laemophloeidae, Gelechiidae, Nitidulidae, Dermestidae, Anobiidae; members of the genus *Cimex*; and members of the species *Armadillidum vulgare*, *Porcellio laevis*, and *Uroblaniulus jersey*.

14. The method of claim 8, wherein the arthropod is selected from a group consisting of members of the order Isoptera and members of the genus *Cimex*.

15. The method of claim 8, wherein the members of the genus *Cimex* are selected from a group consisting of members of the species *Cimex lectularius*.

16. The method of claim 8, wherein the step of applying comprises spraying the insecticidal composition on the target site as an aerosol.

17. The method of claim 8, wherein the step of applying comprises fogging the insecticidal composition at the target site.

* * * * *